United States Patent
Kennedy et al.

(10) Patent No.: US 10,611,734 B2
(45) Date of Patent: Apr. 7, 2020

(54) PROCESS FOR THE PREPARATION OF TRIAZOLES

(71) Applicant: BAYER CROPSCIENCE AKTIENGESELLSCHAFT, Monheim am Rhein (DE)

(72) Inventors: Jason W. J. Kennedy, Köln (DE); Sascha Von Morgenstern, Burscheid (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 8 days.

(21) Appl. No.: 15/552,782

(22) PCT Filed: Feb. 19, 2016

(86) PCT No.: PCT/EP2016/053570
§ 371 (c)(1),
(2) Date: Aug. 22, 2017

(87) PCT Pub. No.: WO2016/135062
PCT Pub. Date: Sep. 1, 2016

(65) Prior Publication Data
US 2018/0050995 A1 Feb. 22, 2018

(30) Foreign Application Priority Data

Feb. 24, 2015 (EP) .................................... 15156316

(51) Int. Cl.
| | | |
|---|---|---|
| *C07D 249/06* | (2006.01) | |
| *C07D 401/04* | (2006.01) | |
| *C07D 401/14* | (2006.01) | |
| *C07C 259/14* | (2006.01) | |
| *C07D 271/06* | (2006.01) | |
| *C07D 213/80* | (2006.01) | |
| *C07D 413/04* | (2006.01) | |
| *C07D 413/12* | (2006.01) | |
| *C07D 413/14* | (2006.01) | |

(52) U.S. Cl.
CPC .......... *C07D 249/06* (2013.01); *C07C 259/14* (2013.01); *C07D 213/80* (2013.01); *C07D 271/06* (2013.01); *C07D 401/04* (2013.01); *C07D 401/14* (2013.01); *C07D 413/04* (2013.01); *C07D 413/12* (2013.01); *C07D 413/14* (2013.01)

(58) Field of Classification Search
None
See application file for complete search history.

(56) References Cited

U.S. PATENT DOCUMENTS

| | | |
|---|---|---|
| 9,802,899 B2 | 10/2017 | Heilmann et al. |
| 2014/0184460 A1 | 7/2014 | Yen |
| 2015/0239847 A1 | 8/2015 | Heilmann et al. |
| 2017/0305864 A1 | 10/2017 | Heilmann et al. |

FOREIGN PATENT DOCUMENTS

| | | | |
|---|---|---|---|
| DE | 1168437 B | 4/1964 | |
| EP | 0350237 A2 | 1/1990 | |
| WO | 0035285 A1 | 6/2000 | |
| WO | 2004014370 A2 | 2/2004 | |
| WO | 2014051055 A1 | 4/2014 | |
| WO | 2014053450 A1 | 4/2014 | |
| WO | WO 2014/053450 * | 4/2014 | ............. A01N 43/56 |
| WO | 2014081689 A1 | 5/2014 | |
| WO | 2014/085490 A1 | 6/2014 | |
| WO | 2014113303 A1 | 7/2014 | |

OTHER PUBLICATIONS

Bottoni et al., The Journal of Physical Chemistry A, vol. 108, No. 10, Mar. 11, 2004, pp. 1731-1740.*
Raders, Steven M., et al., "Trineopentylphosphine: A Conformationally Flexible Ligand for the Coupling of Sterically Demanding Substrates in the Buchwalk-Hartwig Amination and Suzuki-Miyaura Reaction," The Journal of Organic Chemistry, (2013), vol. 78: 4649-4664.
Altenhoff, Gereon, et al., "An N-Heterocyclic Carbene Ligand with Flexible Steric Built Allows Suzuki Cross-Coupling of Sterically Hindered Aryl Chlorides at Room Temperature," Angew. Chem. Int. Ed., (2003), vol. 42: 3690-3693.
Ruiz-Castillo, Paula, et al., "Rational Ligand Design for the Arylation of Hindered Primary Amines Guided by Reaction Progress Kinetic Analysis," Journal of the American Chemical Society, (2015), vol. 137: 3085-3092.
Kathewad, Neha, et al., "Facile Buchwald-Hartwig coupling of sterically encumbered substrates effected by PNP ligands," Dalton Transactions, (2019), vol. 48: 2730-2734.
Navarro, Oscar, et al., "A General Method for the Suzuki-Miyaura Cross-Coupling of Sterically Hindered Aryl Chlorides: Synthesis of Di- and Tri-ortho-substituted Biaryls in 2-Propanol at Room Temperature," Journal of the American Chemical Society, (2003), vol. 125: 16194-16195.
O'Keefe, B. Michael, et al., "Carbonylative Cross-Coupling of ortho-Disubstituted Aryl Iodides. Convenient Synthesis of Sterically Hindered Aryl Ketones," Organic Letters, (2008), vol. 10, No. 22: 5301-5304.
Hill, Lensey L., et al., "Bulky Alkylphosphines with Neopentyl Substituents as Ligands in the Amination of Aryl Bromides and Chlorides," Journal of Organic Chemistry, (2006), vol. 71, No. 14: 5118-5125.
Bottoni, Andrea, et al. Supporting Information for the Paper: Convergent Results from Experimental and Theoretical DFT Studies of the Intra-Molecular Rearrangement of Z-Hydrazones of 3-Acyl-1,2,4-Oxadiazoles, Journal of Physical Chemistry, 2004, p. 1-9, American Cancer Society, US.

(Continued)

*Primary Examiner* — Alicia L Otton
(74) *Attorney, Agent, or Firm* — McBee Moore & Vanik IP, LLC

(57) ABSTRACT

The present invention discloses the efficient preparation of 2-substituted-4-amido-1,2,3-triazoles.

10 Claims, No Drawings

(56) References Cited

OTHER PUBLICATIONS

Begtrup, Mikael et al. Electrophilic and Nucleophilic Substitution in the Triazole N-Oxides and N-Methoxytriazolium Salts: Preparation of Substituted 1,2,3-Triazoles, Jan. 1, 1981, p. 503-511, Lyngby, Denmark.

Ruccia, Michele, et al. Mononuclear Heterocyclic Rearrangements, Advances in Heterocyclic Chemistry, 1981, p. 141-169, vol. 29, Academic Press, Inc.

Nikitin, V.M., et al. Synthesis of 4(5)-Amino-2-Phenyl-1,2,3-Triazoles, Zhurnal Organicheskoi Khimii, 1993, p. 1885-1892, vol. 28, Plenum Publishing Corporation.

Vivona, Nicolo, et al. Ring Transformations of Five-Membered Heterocycles, Advances in Heterocyclic Chemistry, 1993, p. 49-154, vol. 56, Academic Press, Inc.

Ueda, Satoshi, et al. Highly N2-Selective Palladium-Catalyzed Arylation of 1,2,3-Triazoles, Angewandte Chemie Int. Ed., 2011, p. 8944-8947, vol. 50, Wiley-VCH Verlag GmBH & Co. KGaA, Weinheim, Germany.

Albert, Adrien. 4-Amino-1,2,3-triazoles, Advances in Heterocyclic Chemistry, 1986, p. 129-197, vol. 40, Academic Press, Inc.

Deegan, Tracy L., et al. Parallel Synthesis of 1,2,4-Oxadiazoles Using CDI Activation, Bioorganic & Medicinal Chemistry Letters, 1998, p. 209-212, Elsevier Science Ltd., United States.

Gangloff, Anthony R., et al. Synthesis of 3,5-disubstituted-1,2,4-oxadiazoles using tetrabutylammonium fluoride as a mild and efficient catalyst, Tetrahedron Letters, 2001, p. 1441-1443, Elsevier Science Ltd., United States.

Chiou, Shishue, et al. A Simplified Procedure for Preparing 3,5-Disubstituted-1,2,4-Oxadiazoles by Reaction of Amidoximes with Acyl Chlorides in Pyridine Solution, Journal of Heterocyclic Chemistry, 1989, p. 125-128, vol. 26, Lubbock, United States.

Bedford, Clifford D., et al. Nonquaternary Cholinesterase Reactivators. 3. 3(5)-Substituted 1,2,4-Oxadiazol-5(3)-aldoximes and 1,2,4-Oxadiazole-5(3)-thiocarbohydroximates as Reactivators of Organophosphate-Inhibited Eel and Human Acetylcholinesterase in Vitro, Journal of Medicinal Chemistry, 1986, p. 2174-2183, vol. 29, American Chemical Society, United States.

Lamattina, John L., et al. Utility of p-Nitrophenyl 3-Bromo-2,2-diethoxyproponate (NPBDP) in Heterocyclic Synthesis, Journal of Organic Chemistry, 1984, p. 4800-4805, vol. 49, American Chemical Society, United States.

Bailey, Nick, et al. Solution-Phase Combinatorial Chemistry in Lead Discovery, Chimia, 1997, p. 832-837, vol. 61, Neue Schweizerische Chemische Gesellschaft.

Palazzo, G. 1,2,4-Oxadiazoles. X (1). Aryl-1,2,4-oxadiazolecarbaldehydes, Journal of Heterocyclic Chemistry, 1979, p. 1469-1475, vol. 16, Turin, Italy.

Cosimelli, Barbara, et al. The First Kinetic Evidence for Acid Catalysis in a Monocyclic Rearrangement of Heterocycles: Conversion of the Z-Phenylhydrazone of 5-Amino-3-benzoyl-1,2,4-oxadiazole into N,5-Diphenyl-2-H-1,2,3-triazol-4-ylurea, Journal of Organic Chemistry, Nov. 23, 2002, p. 8010-8018, vol. 67, American Chemical Society, Turin, Italy.

D'Anna, Francesca. On the Dichotomic Behavior of the Z-2,4-Dinitrophenylhydrazone of 5-Amino-3-benzoyl-1,2,4-oxadiazole with Acids in Toluene and in Dioxane/Water: Rearrangement versus Hydrolysis, Journal of Organic Chemistry, 2004, p. 8718-8722, vol. 69, American Chemical Society, Italy.

Spinelli, Domenico, et al. Mononuclear Heterocyclic Rearrangements. Part 2.1c Substituent Effects on the Rate of Rearrangement of Some Arylhydrazones of 3-Benzoyl-5-phenyl-1,2,4-oxadiazole into 2-Aryl-4-benzoylamino-5-phenyl-1,2,3-triazole, at pS+ 3.80, Journal of Chemical Society Perkin 2, 1978, p. 19-22, Italy.

Buscemi, Silvestre, et al. Copper(II)-catalyzed Molecular Rearrangements: the Behaviour of Arylhydrazones of some 3-Benzoylazoles in the Presence of Copper(II) Acetate, Journal of Chemical Society Perkin Trans. 1, 1993, p. 2491-2493, Italy.

Vivona, et al., "Mononuclear Heterocyclic Rearrangements. Part 4 (1). Synthesis and Characterization of the E-isomer Phenylhydrazone of 3-Benzoyl-5-phenyl-1,2,4-oxadiazole," J. Heterocyclic Chem., (1980), vol. 17:401.

Frenna, et al., "Mononuclear Heterocyclic Rearrangements. Part 16. Kinetic Study of the Rearrangement of Some ortho-Substituted Z-Phenylhydrazones of 3-Benzoyl-5-phenyl-1,2,4-oxadiazole into 2-Aryl-4-benzoylamino-5-phenyl-1,2,3-triazoles in Dioxane-Water and in Benzene," Tetrahedron, (1999), vol. 55: 12885-12896.

\* cited by examiner

PROCESS FOR THE PREPARATION OF TRIAZOLES

CROSS REFERENCE TO RELATED APPLICATIONS

This application is a § 371 National State Application of PCT/EP2016/053570, filed Feb. 19, 2016, which claims priority to European Application No. 15156316.0 filed Feb. 24, 2015.

BACKGROUND OF THE INVENTION

Field of the Invention

The present invention discloses the efficient preparation of 2-substituted-4-amido-1,2,3-triazoles.

Description of Related Art

2-Substituted-4-amido-1,2,3-triazoles are class of heterocycles that have demonstrated important applications as, for example, pest control agents (e.g., structure 1a, WO 2014/053450 A1) or pharmaceuticals (e.g., structure 1b, WO 2014/051055 A1).

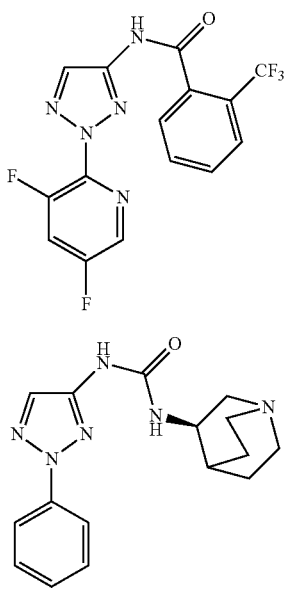

Despite these useful properties, a simple and efficient procedure for the large scale preparation of these compounds has not yet been developed. While 4-amido-1,2,3-triazoles are readily prepared by standard acylation of 4-amino-1,2,3-triazoles, these amino-derivatives are themselves difficult to prepare. Several syntheses of 4-amino-1,2,3-triazoles have been reported based on the introduction of the 4-amino group to a pre-existing 1,2,3-triazole, such as via the Curtius rearrangement (WO 2014/053450 A1, WO 2014/051055 A1), or by addition of a nitrogen nucleophile to a suitably activated triazole according to the procedure of Begtrup and co-workers (*J. Chem. Soc. Perkin Trans.* 1, 1981, 503-513). These syntheses tend to be long and involve energetic or exotic compounds that are not conveniently handled in technical scale reactions.

Scheme 1: 4-Amino-1,2,3-triazoles via the procedure of Begtrup and co-workers

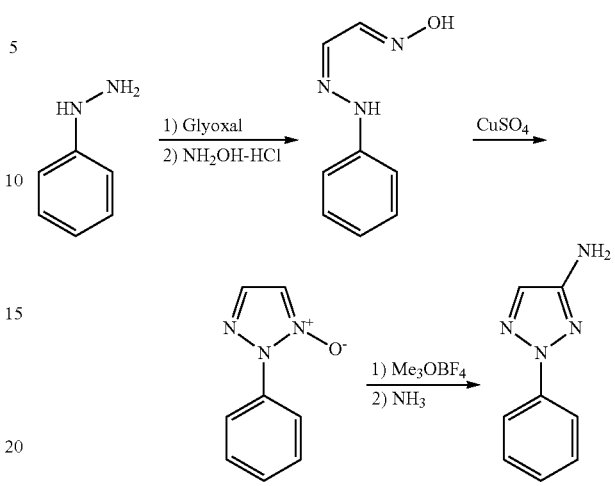

Nikitin and co-workers have described a preparation of 2-phenyl-4-amino-1,2,3-triazole by the reduction of the corresponding 4-nitrotriazole (*Zh. Obshchei. Khim.* 1992, 28, 2334-2343), which could then be acylated to the corresponding 4-amido-1,2,3-triazole by a variety of methods known to one skilled in the art. This intermediate amine can be prepared by reaction of an aryl diazonium salt with the extremely sensitive methazonic acid (DE1168437). Although reasonably short, this route also involves energetic chemistry and reactive intermediates that would be challenging to handle safely in large-scale campaigns.

O'Mahony and co-workers have reported preparations of 4-amino-1,2,3-triazoles from oximinohydrazones, either via metal-mediated oxidation or via oxime-acylation (*Pestic. Sci.* 1996, 48, 189-196; EP 0 350 237 A2). In addition to passing though some highly energetic intermediates, these preparations involve exotic reagents or stoichiometric amounts of metal oxidant, which leads to expensive or difficult to handle waste.

Alternatively, Dimroth cyclization between an aryl azide and a cyanomethylene compound (Albert, A. *Adv. Heterocycl. Chem.* 1986, 40, 129-197) delivers a 1-aryl-2-amino-1,2,3-triazole that can be converted over several steps to a 2-unsubstituted-4-amino-1,2,3-triazole (WO 2014/081689 A1). Modern, metal-catalysed C—N bond formation reactions have been used to prepare 2-arylated-1,2,3-triazoles from similar intermediates (WO 2014/113303 A1; Buchwald, et al. *Angew. Chem. Int. Ed. Int.* 2011, 50, 8944-9747). These C—N couplings, however, are generally not suitable for the preparation of technical amounts of product because they either require expensive catalysts (e.g., Buchwald, et al. *J. Org. Chem.* 2012, 77, 2543-2547) or show poor selectivity in the coupling (e.g., Baxter, et al. *Org. Process Res. Dev.* 2011, 15, 367-375).

In general, the above described syntheses are long, inefficient, and require chemistry or reagents that are disadvantageous for large scale productions from a safety, economical, or environmental point of view. As such there is still an unmet need for a general, simple, and scalable synthesis of 2-substituted-4-amido-1,2,3-triazoles that are unsubstituted in the 5-position.

SUMMARY

This problem was solved by inventing a direct and efficient preparation of 2-substituted-4-amido-1,2,3-triazoles that starts from readily available compounds and does not rely on expensive catalysts or energetically unfavourable azide or diazotization methodologies. 3-Carbonohydrazonoyl-1,2,4-oxadiazoles derived from a phenyl ketone (e.g., compounds with the general structure 2) are known to give 4-amido-5-phenyl-1,2,3-triazoles (compounds of the general structure 5) via the Boulton-Katritzky rearrangement (Spinelli, D., et al. *Adv. Heterocycl. Chem.* 1981, 29, 141-169). Although the preparation of such phenyl-substituted derivatives is well documented, there were only vague reports without details that a 5-methyl-triazole has been prepared via this chemistry (e.g., rearrangements of hydrazones of the general structure 3 to 1,2,3-triazoles of the general structure 6; Vivona, et al. *Adv. Heterocycl. Chem.* 1993, 56, 50-154), and there was surprisingly no precedent for the use of aldehyde-derived hydrazones (compounds of the general structure 4), which would lead to 5-unsubstituted triazoles (compounds of the general structure 1).

tuted-4-amido-1,2,3-triazioles of the general structure 1 via Boulton-Katritzky rearrangement of a 3-carbonohydrazonoyl-1,2,4-oxadiazole of the general structure 4. There is a complete absence of examples involving aldehyde-derived hydrazones in the three decades since the first reports of this rearrangement. Surprisingly it was now found that hydrazonyl oxadiazoles of the general structure 4 can participate in an efficient Boulton-Katritzky rearrangement, leading to good yields of 4-amido-1,2,3-triazoles of formulae 1 that are unsubstituted in the 5-position. This preparation proceeds from simple starting materials and avoids energetically unfavourable diazotization or azide chemistry.

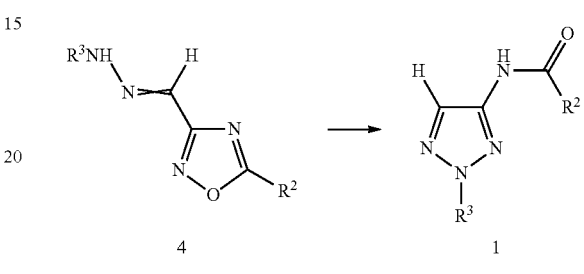

4            1

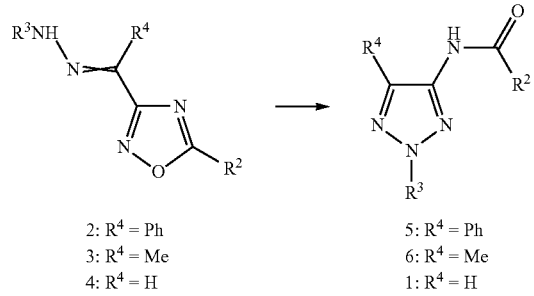

2: R⁴ = Ph     5: R⁴ = Ph
3: R⁴ = Me    6: R⁴ = Me
4: R⁴ = H      1: R⁴ = H

DETAILED DESCRIPTION OF A PREFERRED EMBODIMENT

The present invention describes the unexpectedly straightforward and convenient preparation of 5-unsubsti- The synthesis described in this invention starts with the preparation of an amidoxime of the general structure 8 via the addition of hydroxylamine to a nitrile bearing a protected aldehyde of the general structure 7. Reaction of the amidoxime 8 with a suitable acylating agent 9 leads to the amidoxime ester 10 that can then be cyclized to the oxadiazole 11. Cleavage of the protecting group in 11 to the aldehyde 12 followed by condensation with an organic hydrazine of the general structure 13 gives a hydrazone of the general structure 4, generally present as a mixture of E- and Z-isomers. Finally, Boulton-Katritzky rearrangement of such hydrazones delivers the desired 4-amido-1,2,3-triazoles of the general structure 1.

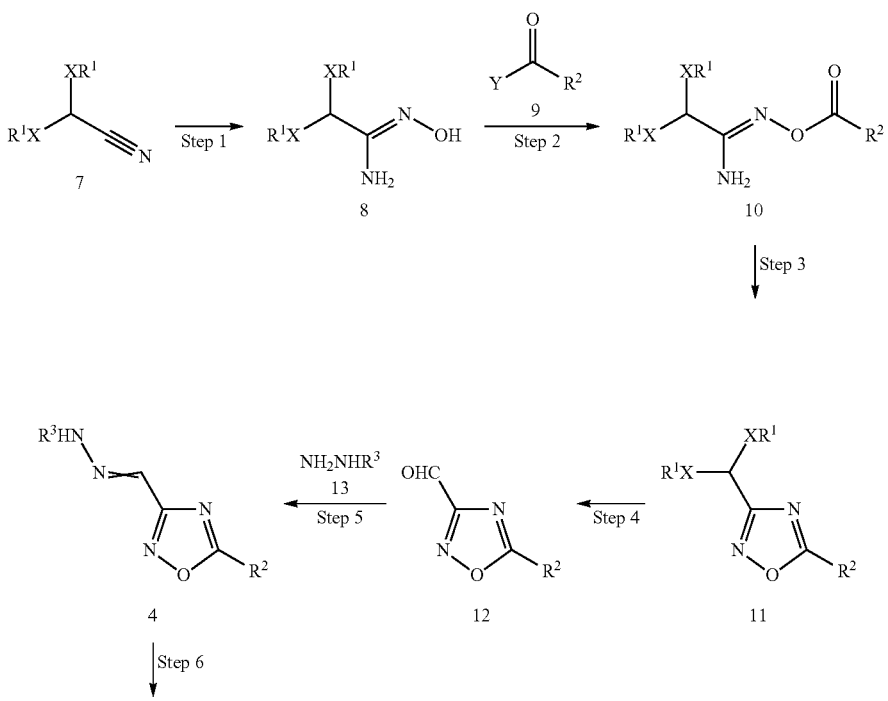

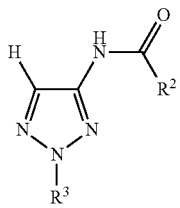

1

Alternatively, the efficiency of this process can be increased by performing the last two or three steps in a convenient, one-pot, multi-step sequence, allowing for rapid conversion of either the protected oxadiazole 11 or the aldehyde 12 to the triazole 1 without isolation of the corresponding intermediates.

The first step of the process according to the present invention is the preparation of an amidoxime of the general structure 8 from a nitrile of the general structure 7

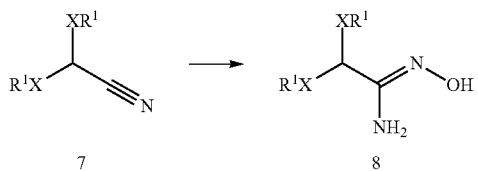

wherein
X is either sulfur or oxygen;
$R^1$ is $C_{1-8}$-alkyl (which may be straight-chained, cyclic, or branched), phenyl (which is unsubstituted or is substituted with 1-5 groups independently chosen from the following list: $C_{1-8}$-alkyl groups (which may be straight-chained, cyclic, or branched), halogens, $C_{1-4}$-alkoxy (which may be straight-chained or branched), or nitro groups). Alternatively the two $R^1$-groups may be joined by a $C_{1-3}$-alkyl group or be part of a 1,2-disubstituted phenyl group to form a cyclic unit. This cyclic unit may be further substituted with 1-6 groups chosen from the following list: $C_{1-6}$-alkyl groups (which may be straight-chained, cyclic, or branched), halogens, benzyl, trimethylsilyl, acetoxy, phenyl, 4-methoxyphenyl, 2-nitrophenyl, $C_{1-4}$-alkoxycarbonyl (which may be straight-chained or branched), carboxylic acids, or groups of the structure $C(=O)NR^aR^b$ (where $R^a$ and $R^b$ are independently chosen between H or a $C_{1-4}$-alkyl group (which may be straight-chained or branched)).

In this and the following embodiments the terms "straight-chained, cyclic, or branched" are only relevant to groups with more than two carbon atoms.

In a preferred embodiment of the invention
X is oxygen;
$R^1$ is $C_{1-4}$-alkyl (which may be straight-chained or branched), phenyl (which is unsubstituted or is substituted with 1-2 groups independently chosen from the following list: $C_{1-4}$-alkyl groups (which may be straight-chained or branched), halogens, $C_{1-4}$-alkoxy (which may be straight-chained or branched), or nitro groups). Alternatively the two $R^1$-groups may be joined by a $C_{1-3}$-alkyl group or be part of a 1,2-disubstituted phenyl group to form a cyclic unit. This cyclic unit may be further substituted with 1-4 groups independently chosen from the following list: $C_{1-6}$-alkyl (which may be straight-chained, cyclic, or branched), $C_{1-4}$-alkoxycarbonyl (which may be straight-chained or branched), or groups of the structure $C(=O)NR^aR^b$ (where $R^a$ and $R^b$ are independently chosen between H and a $C_{1-4}$-alkyl group (which may be straight-chained or branched)).

In an especially preferred embodiment of the invention
X is oxygen;
$R^1$ is $C_{1-4}$-alkyl (which may be straight-chained or branched). Alternatively the two $R^1$-groups may be joined by a $C_{1-3}$-alkyl group to form a cyclic unit. This cyclic unit may be further substituted with 1-4 groups independently chosen from the following list: $C_{1-4}$-alkyl groups (which may be straight-chained or branched), $C_{1-4}$-alkoxycarbonyl groups (which may be straight-chained or branched), or groups of the structure $C(=O)NR^aR^b$ (where $R^a$ and $R^b$ are independently chosen between H and a $C_{1-4}$-alkyl group (which may be straight-chained or branched)).

The amidoxime can be prepared in analogy to procedures already known in the literature using analogous nitriles (e.g., LaMattina, J. L. et al., *J. Org. Chem.* 1984, 49, 4800-4805; WO 2013/171318 A1). The Z-stereochemistry of the amidoxime depicted in structure 8 has not been confirmed by experimental data. A person skilled in the art will recognize that amidoximes can exist as E- and Z-isomers and that these isomers can interconvert (Dondoni, A., et al. *J. Org. Chem.* 1975, 40, 2979-2980). The present invention includes the preparation and use of either of these isomeric forms and mixtures thereof. For the sake of clarity in the text, only one of the potential isomers is shown for amidoximes of the general formula 8.

The second step of the process is the acylation of an amidoxime of the general structure 8 with an acylating agent 9 to give a novel compound with the general structure 10

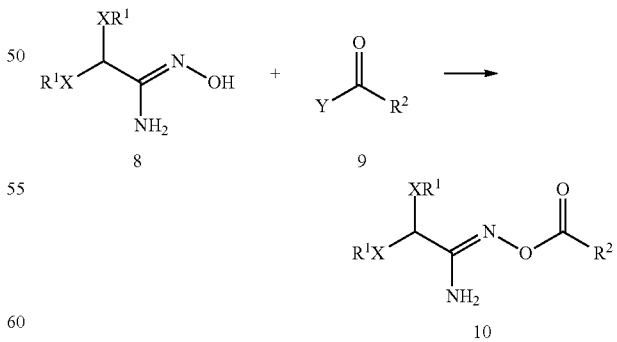

wherein X and $R^1$ have the same definitions as provided above for the preparation of compounds of the general structure 8, and;
Y is a halogen, OH, a $C_{1-4}$-alkoxy group (which may be straight-chained or branched), a phenoxy group (which is unsubstituted or is substituted with 1-5 substituents independently chosen from the following list: $C_{1-4}$-alkyl (which may be straight-chained or branched), halogen, or nitro), or a group of the formula $R^ZC(=O)O$, where either $R^Z$ is the same as $R^2$, or $R^Z$ is a $C_{1-8}$-alkyl group (which may be straight-chained, cyclic, or branched), or a $C_{1-8}$-haloalkyl group (which may be straight-chained, cyclic, or branched); $R^2$ is an alkyl, aromatic, or heterocyclic group.

When $R^2$ is an alkyl group, it is a $C_{1-8}$-group (which may be straight-chained or branched), and may contain 1-17 groups chosen independently from the following list: halogens, $C_{1-8}$-alkoxy groups (which may be straight-chained, cyclic, or branched), $C_{1-8}$-alkylthio groups (which may be straight-chained, cyclic, or branched), nitrile or groups of the structure $C(=O)NR^aR^b$ (where $R^a$ and $R^b$ are independently chosen between H and a $C_{1-4}$-alkyl group (which may be straight-chained or branched)). Alternatively $R^2$ is a $C_{3-6}$-carbocycle that can be substituted with 1-6 groups independently chosen from the following list: $C_{1-4}$-alkyl groups (which may be straight-chained, cyclic, or branched), $C_{1-4}$-alkoxy groups (which may be straight-chained, cyclic, or branched), halogen, $C_{1-4}$-alkoxycarbonyl groups (which may be straight-chained or branched), $C_{1-8}$-alkylthio groups (which may be straight-chained, cyclic, or branched), nitriles or groups of the structure $C(=O)NR^aR^b$ (where $R^a$ and $R^b$ are independently chosen between H and a $C_{1-4}$-alkyl group (which may be straight-chained or branched)).

When $R^2$ is an aromatic group, it is a phenyl, naphthyl, anthracenyl, phenanthrenyl, or pyrenyl group, and is unsubstituted or is substituted with 1-5 substituents independently chosen from the following list: $C_{1-8}$-alkyl groups (which may be straight-chained, cyclic, or branched), $C_{1-8}$-haloalkyl groups (which may be straight-chained, cyclic, or branched), $C_{1-8}$-alkoxy groups (which may be straight-chained, cyclic, or branched), $C_{1-8}$-alkylthio groups (which may be straight-chained, cyclic, or branched), halogens, nitro groups, nitrile groups, or groups of the structure $C(=O)NR^aR^b$ (where $R^a$ and $R^b$ are independently chosen between H and a $C_{1-4}$-alkyl group (which may be straight-chained or branched)).

When $R^2$ is heterocyclic, is a 4-, 5-, or 6-membered ring containing 1-4 heteroatoms independently chosen between O, N, and S. This heterocycle is unsubstituted or is substituted with 1-4 substituents independently chosen from the following list: $C_{1-8}$-alkyl groups (which may be straight-chained, cyclic, or branched), $C_{1-8}$-haloalkyl groups (which may be straight-chained, cyclic, or branched), $C_{1-8}$-alkoxy groups (which may be straight-chained, cyclic, or branched), $C_{1-8}$-alkylthio groups (which may be straight-chained, cyclic, or branched), nitriles, nitro groups, halogens, or groups of the structure $C(=O)NR^aR^b$ (where $R^a$ and $R^b$ are independently chosen between H or a $C_{1-4}$-alkyl group (which may be straight-chained or branched)).

In a preferred embodiment of the invention, X and $R^1$ have the same definitions as provided above for the preferred embodiment of the preparation of compounds of the general structure 8, and
Y is a halogen, or a group of the formula $R^ZC(=O)O$, where $R^Z$ is the same as $R^2$, or $R^Z$ is a $C_{1-4}$-alkyl group (which may be straight-chained or branched), or a $C_{1-4}$-haloalkyl group (which may be straight-chained or branched);
$R^2$ is an alkyl, aromatic, or heterocyclic group.

When $R^2$ is an alkyl group, it is a $C_{1-4}$-group (which may be straight-chained or branched), and may contain 1-9 groups independently chosen from the following list: halogens, $C_{1-4}$-alkoxy groups (which may be straight-chained, cyclic, or branched), or groups of the structure $C(=O)$ $NR^aR^b$ (where $R^a$ and $R^b$ are independently chosen between H and a $C_{1-4}$-alkyl group (which may be straight-chained or branched)). Alternatively $R^2$ is a $C_{3-6}$-carbocycle that can also be substituted with 1-4 groups independently chosen from the following list: $C_{1-4}$-alkyl groups (which may be straight-chained, cyclic, or branched), $C_{1-4}$-alkoxy groups (which may be straight-chained, cyclic, or branched), $C_{1-4}$-haloalkyl groups (which may be straight-chained, cyclic, or branched), or halogens.

When $R^2$ is aromatic group, it is a phenyl, naphthyl, or anthracenyl group, and is unsubstituted or is substituted with 1-4 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), halogens, nitro groups, nitrile groups, or groups of the structure $C(=O)NR^aR^b$ (where $R^a$ and $R^b$ are independently chosen between H and a $C_{1-4}$-alkyl group (which may be straight-chained or branched)).

When $R^2$ is heterocyclic, it is a 4-, 5-, or 6-membered ring containing 1-4 heteroatoms independently chosen between O, N, and S, and is in particular selected from the group consisting of

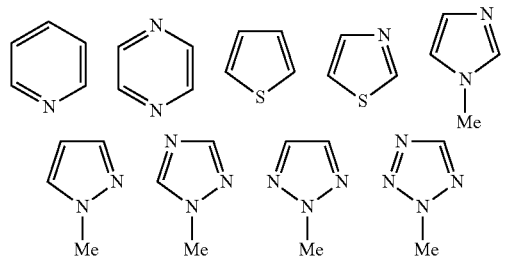

which may be connected to the rest of the molecule through any of the ring carbon atoms. This heterocycle is unsubstituted or is substituted with 1-3 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained or branched), nitriles, nitro groups, halogens, or groups of the structure $C(=O)NR^aR^b$ (where W and $R^b$ are independently chosen between H or a $C_{1-4}$-alkyl group (which may be straight-chained or branched)).

In an especially preferred embodiment of the invention, X and $R^1$ have the same definitions as provided above for the especially preferred embodiment of the preparation of compounds of the structure 8, and
Y is a halogen or a group of the formula $R^ZC(=O)O$, where $R^Z$ is the same as $R^2$;
$R^2$ is an alkyl, aromatic or heterocyclic group.

When $R^2$ is an alkyl group, it is a $C_{1-4}$-group (which may be straight-chained or branched), and may contain halogens. Alternatively $R^2$ is $C_{3-6}$-carbocycle that can be substituted with 1-3 groups independently chosen from the following list: $C_{1-4}$-alkyl groups (which may be straight-chained, cyclic, or branched), $C_{1-4}$-alkoxy groups (which may be straight-chained, cyclic, or branched), $C_{1-4}$-haloalkyl groups (which may be straight-chained, cyclic, or branched), or halogens.

When $R^2$ is an aromatic group, it is a phenyl group, and is unsubstituted or is substituted with 1-3 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), halogens, nitro groups, nitrile groups.

When $R^2$ is heterocyclic, it is a pyridine ring; a pyrazine ring; a thiophene ring; a thiazole ring, or a 1-methylpyrazole ring. This heterocycle is unsubstituted or is substituted with 1-2 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), nitriles, or halogens.

When Y is a halogen or a group of the formula $R^ZC(=O)$O, the acylation may be optionally performed in the presence of a base such as an aliphatic amine (e.g., triethylamine (NEt$_3$), Hünig's base), an aromatic amine (e.g., pyridine, N,N-dimethylaminopyridine (DMAP)), or an inorganic base (e.g., alkali metal hydroxides, carbonates, or bicarbonates).

When Y is a halogen or a group of the formula $R^ZC(=O)$O, the acylation reaction between an amidoxime of formula 8 and an acylating agent of formula 9 may be performed neat or in the presence of a solvent. In reactions where a solvent is used, solvents such as amides (e.g., N,N-dimethylformamide (DMF), N,N-dimethylacetamide (DMAC)), nitriles (e.g., acetonitrile (MeCN), butyronitrile (PrCN)), ethers (e.g., diethyl ether (Et$_2$O), 2-methyltetrahydrofuran, tetrahydrofuran (THF), methyl (t)-butyl ether (MTBE)), esters (e.g., ethyl acetate (EtOAc), butyl acetate (BuOAc)), aromatic hydrocarbons or halogenated derivatives thereof (e.g., toluene, xylene, chlorobenzene), hydrocarbons or halogenated derivatives thereof (e.g., methylcyclohexane, dichloromethane, dichloroethane), sulfoxides (e.g., dimethylsulfoxide, sulfolane), ketones (e.g., acetone, methylisobutylketone), or water may be used either singly or as a mixture of two or more thereof. The use of halogenated hydrocarbons, nitriles, ethers, aromatic hydrocarbons, or mixtures thereof is preferred.

When Y is OH, the acylation may be performed with a dehydrating agent (e.g., POCl$_3$, SOCl$_2$, N,N'-dicyclohexylcarbodiimide (DCC), 1-ethyl-3-(3-dimethylaminopropyl)-carbodiimide (EDCI), N-hydroxybenzotriazole (HOBT), 1-hydroxy-7-azabenzotriazole (HOAT)). Optionally, acylation of compounds of the general structure 8 using a reagent of the general structure 9 where Y is OH can be performed in the presence of one of the bases and or solvents described above for the use of an acylating reagent of the general structure 9 where Y is a halogen or a group of the formula $R^ZC(=O)O$. Acylation of amidoximes analogous to those represented by the general structure 8 with carboxylic acids has been reported by Merritt and co-workers (*Chimia*, 1997, 51, 832-837).

The reaction stoichiometry between amidoximes of formulae 8 and reagents of formulae 9 may range from 0.1 equiv. to 5 equiv., although a range from 0.5-1.5 equiv. is preferred.

The reaction may be carried out between –40° C. and 150° C., and is preferably carried out between –10° C. and 120° C.

The reaction may be carried out between 0.1 bar and 10 bar pressure, and is preferably carried out between 0.8 bar and 1.2 bar.

The Z-stereochemistry of the acylated amidoxime depicted in structure 10 has not been confirmed by experimental data. A person skilled in the art will recognize that such compounds can exist as E- and Z-isomers and that these isomers can interconvert. The present invention includes the preparation and use of either isomeric form and mixtures thereof. For the sake of clarity in this text, only one of the potential isomers is shown for compounds of formula 10.

The third step in the process is the cyclization of an acylated amidoxime of structure 10 to a 1,2,4-oxadiazole of structure 11

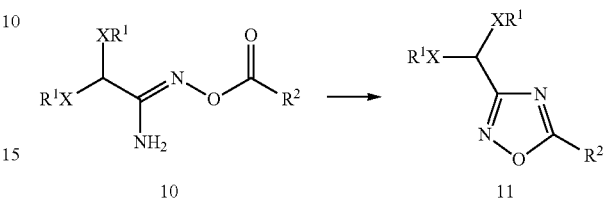

wherein X, $R^1$, and $R^2$ have the same definitions as provided above for the preparation of acylated amidoximes of the general formula 10.

In a preferred embodiment of the invention, X, $R^1$, and $R^2$ have the same definitions as provided above for the preferred embodiment of the preparation of acylated amidoximes of the general formula 10.

In an especially preferred embodiment of the invention, X, $R^1$, and $R^2$ have the same definitions as provided above for the especially preferred embodiment of the preparation of acylated amidoximes of the general formula 10.

Cyclization to analogous oxadiazoles can be effected under thermal conditions following the procedure of Bedford and co-workers (*J. Med. Chem.* 1986, 29, 2174-2183), basic conditions according to the procedure of Chiou and Shine (*J. Heterocycl. Chem.* 1989, 26, 125-128), acidic conditions (WO 2010/123451 A1), or in the presence of a dehydrating agent such as 1,1'-carbonyldiimidazole (CDI) according to the procedure of Porco and co-workers (*Bioorg. Med. Chem. Lett.* 1999, 9, 209-212). Alternatively the cyclization can be achieved using substoichiometric amounts of tetra-(n)-butylammonium fluoride (TBAF) according to the procedure of Gangloff and co-workers (*Tetrahedron Lett.* 2001, 42, 1441-1443). Preferred is to achieve the cyclization in the presence of TBAF. Based on the work of Gangloff and co-workers, one skilled in the art would expect that this cyclization should also be achievable in the presence of other fluoride sources (e.g., KF).

The fourth step in the process is the cleavage of the protecting group in the oxadiazole of the general structure 11 to give an aldehyde of structure 12

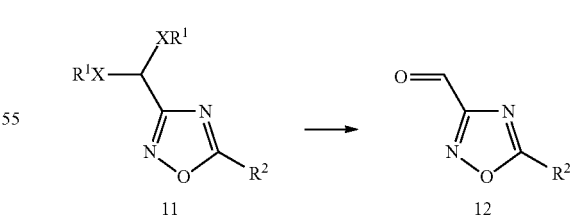

wherein X, $R^1$, and $R^2$ have the same definitions as provided above for the preparation of protected oxadiazoles of the general formula 11.

In a preferred embodiment of the invention, X, $R^1$, and $R^2$ have the same definitions as provided above for the preferred embodiment of the preparation of protected oxadiazoles of the general formula 11.

In an especially preferred embodiment of the invention, X, $R^1$, and $R^2$ have the same definitions as provided above for the especially preferred embodiment of the preparation of protected oxadiazoles of the general formula 11.

The reaction may be performed using a procedure for the cleavage of acetals and thioacetals such as those described by Greene and Wuts (Greene, T. W.; Wuts, P. G. M. Protective Groups in Organic Synthesis, $3^{rd}$ ed.; John Wiley & Sons: New York, 1999). Preferred is the use of mineral acids (e.g., HCl, $H_2SO_4$, $H_3PO_4$) or an organic acid (e.g., $CF_3CO_2H$, $CH_3SO_3H$, $CF_3SO_3H$, p-toluenesulfonic acid (pTSA)) in a solvent such as MeCN, toluene, THF, water, or in a mixture comprised of two or more of these solvents.

Plazzo and co-workers (J. Heterocycl. Chem. 1979, 16, 1469-1475) reported that aldehydes of the general structure 12 readily form stable hydrates of the general structure 14, and that these hydrated forms display the same chemical reactivity as the free aldehyde form 12. The present invention should be understood to include the preparation or use of either the aldehyde form 12 or the corresponding hydrate form 14 in the preparation of 5-unsubstituted-4-amido-1,2,3-triazoles of the general structure 1. For clarity generally only the aldehyde form 12 is shown in the schemes and figures in this text.

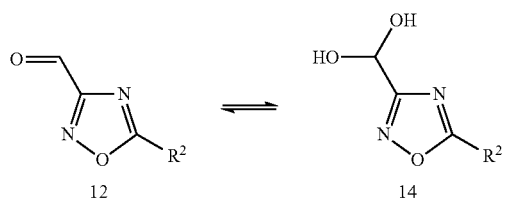

Alternative synthetic routes to aldehydes represented by structure 12 include the reduction of the corresponding ester (WO 2004/014370 A2) or oxidation of the corresponding alcohol (US 20140184460 A1). Such aldehydes can also be prepared via a multi-step process from 3-chloromethyl-1,2,4-oxadiazoles (Plazzo, G. et al. J. Heterocycl. Chem. 1979, 16, 1469-1475). One skilled in the art will appreciate that these alternative procedures are longer than the above described synthesis, or require reagents that are not readily applied in large scale reactions because of high costs, difficult to handle waste products, or safety concerns during the reaction.

The fifth step of the process is the conversion of an aldehyde of the structure 12 to a novel hydrazone of the structure of 4:

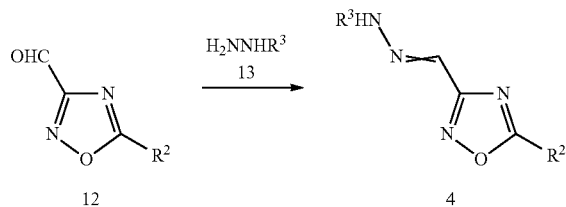

wherein $R^2$ has the same definition as provided above for the preparation of aldehydes of the general formula 12, and $R^3$ is an alkyl, aromatic or heterocyclic group.

When $R^3$ is an alkyl group, it is a $C_{1-8}$-group (which may be straight-chained or branched), and may contain 1-17 substituents independently chosen from the following list: $C_{1-4}$-alkoxy groups (which may be straight-chained, cyclic, or branched), halogen, or $C_{1-4}$-alkoxycarbonyl groups (which may be straight-chained or branched). Alternatively $R^3$ is a $C_{3-6}$-carbocycle that can be substituted with 1-5 groups independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), $C_{1-4}$-alkoxycarbonyl groups (which may be straight-chained or branched), or halogens.

When $R^3$ is an aromatic group, it is a phenyl, naphthyl, anthracenyl, phenanthrenyl, or pyrenyl group, and is unsubstituted or is substituted with 1-5 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), $C_{1-4}$-alkoxycarbonyl groups (which may be straight-chained or branched), groups of the structure $C(=O)NR^aR^b$ (where $R^a$ and $R^b$ are independently chosen between H or a $C_{1-4}$-alkyl group (which may be straight-chained or branched)), nitro groups, nitriles, or halogens.

When $R^3$ is heterocyclic, it is 4-, 5-, or 6-membered ring containing 1-4 heteroatoms independently chosen between O, N, and S. This heterocycle is unsubstituted or is substituted with 1-4 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), $C_{1-4}$-alkoxycarbonyl groups (which may be straight-chained or branched), groups of the structure $C(=O)NR^aR^b$ (where $R^a$ and $R^b$ are independently chosen between H or a $C_{1-4}$-alkyl group (which may be straight-chained or branched)), nitro groups, nitriles, or halogens.

In a preferred embodiment of the invention $R^2$ has the same definitions as provided above for the preferred embodiment of the preparation of aldehydes of the general formula 12, and $R^3$ is an alkyl, aromatic or heterocyclic group.

When $R^3$ is an alkyl group, it is a $C_{1-4}$-group (which may be straight-chained or branched), and may contain 1-9 halogens. Alternatively it is a $C_{3-6}$-carbocycle that can be substituted with 1-3 groups independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), or halogens.

When $R^3$ is an aromatic group, it is a phenyl, naphthyl, or anthracenyl group, and is unsubstituted or is substituted with 1-4 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), nitro groups, nitriles, or halogens.

When $R^3$ is heterocyclic, it is a 4-, 5-, or 6-membered ring containing 1-4 heteroatoms independently chosen between O, N, and S, and is in particular selected from the group consisting of

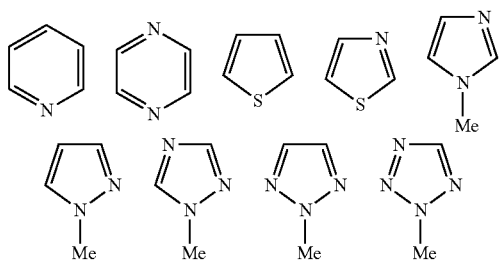

which may be connected to the rest of the molecule through any of the ring carbon atoms. This heterocycle is unsubstituted or is substituted with 1-3 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), nitro groups, nitriles, or halogens.

In an especially preferred embodiment of the invention $R^2$ has the same definitions as provided above for the especially preferred embodiment of the preparation of aldehydes of the general formula 12, and $R^3$ is an alkyl, aromatic or heterocyclic group.

When $R^3$ is an alkyl group, it is a $C_{1-4}$-group (straight-chained or branched) and may contain 1-9 halogens. Alternatively it is a $C_{3-6}$-carbocycle that can also be substituted with 1-2 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), or halogens.

When $R^3$ is an aromatic group, it is a phenyl group, and is unsubstituted or is substituted with 1-3 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), nitro groups, nitriles, or halogens.

When $R^3$ is heterocyclic, it is a pyridine ring; a pyrazine ring; a thiophene ring; a thiazole ring, or a 1-methylpyrazole ring. This heterocycle is unsubstituted or is substituted with 1-2 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), nitriles, or halogens.

The reaction may be performed using a free hydrazine of the general structure 13 or using a salt of such a hydrazine. When such a salt is used, it may be a hydrochloride, hydrobromide, sulfate, acetate, trifluoroacetate, methanesulfonate, or 4-toluenesulfonate salt of a hydrazine of the general structure 13. Preferred is the use of a free hydrazine or a hydrochloride salt thereof.

One skilled in the art will be aware that the condensation of an aldehyde of the structure 12 with a hydrazine of the structure 13 (or corresponding salt thereof) can be performed neat or in various solvents, such as MeCN, water, toluene, or THF, and that the reaction can optionally be performed in the presence of an acid (e.g., HCl, $H_2SO_4$, HOAc, pTSA, $MeSO_3H$).

One skilled in the art will further be aware that hydrazones of the general structure 4 can exist as E- or Z-isomers, and that these isomers can interconvert. If desired, these isomers can generally be separated by standard isolation techniques (e.g., chromatography, recrystallization, distillation). The present invention includes the preparation and use of either of these isomeric forms and mixtures thereof.

In a more efficient embodiment of this invention, hydrazones of the general structure 4 can be prepared directly from the protected oxadiazole 11 in a two-step sequence without isolation of the intermediate aldehyde 12. This tandem sequence is especially preferred when the corresponding intermediate aldehyde is difficult or inconvenient to isolate.

The sixth step of the process is the conversion of a hydrazone of the general structure 4 to a 1,2,3-triazole of the general structure 1

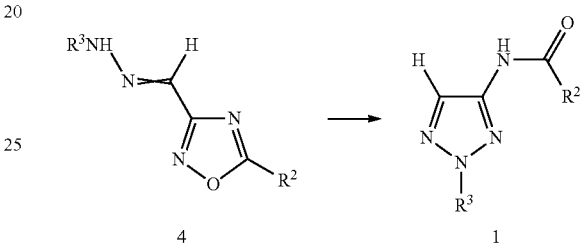

wherein $R^2$ and $R^3$ have the same definitions as provided above for the preparation of hydrazones of the general structure 4.

In a preferred embodiment of the invention $R^2$ and $R^3$ have the same definitions as provided above for the preferred embodiment of the preparation of hydrazones of the general structure 4.

In an especially preferred embodiment of the invention $R^2$ and $R^3$ have the same definitions as provided above for the especially preferred embodiment of the preparation of hydrazones of the general structure 4.

This rearrangement has been demonstrated with hydrazones derived from phenyl ketones (structures analogous compounds of the general formula 1, where the explicitly shown hydrogen atom on the imine carbon has been replaced with a phenyl group). The reaction with these phenyl analogues has been achieved under thermal (Spinelli, et al. *J. Chem. Soc. Perkin Trans.* 2, 1978, 19-22), basic (Spinelli, et al. *J. Org. Chem.* 2002, 67, 8010-8018), or acidic conditions (Spinelli, et al. *J. Org. Chem.* 2004, 69, 8718-8722), as well as in the presence of a Lewis acid catalyst (Spinelli, et al. *J. Chem. Soc. Perkin Trans.* 1, 1993, 2491-2493).

Surprisingly, over the three decades since the first reports of this rearrangement, not a single example has been reported using aldehyde-derived hydrazones of the structure 4. We found that these significantly more labile, aldehyde-derived hydrazones of the general structure 4 undergo an unexpectedly efficient and smooth rearrangement to 1,2,3-triazoles of the general structure 1 under thermal conditions or in the presence of an activating agent. Suitable activating agents for the rearrangement include inorganic bases (e.g., alkali metal hydroxides, carbonates or bicarbonates), alkali metal salts of simple alcohols (e.g., MeONa, (t)-BuOK, EtONa), aliphatic or aromatic amines (e.g., $NEt_3$, Hünig's base, $Bu_3N$, DBU, pyridine, DMAP), strong acids (e.g., HCl, $H_2SO_4$, $CH_3SO_2H$, pTSA, $CF_3CO_2H$, $CF_3SO_3H$), and copper salts (CuCl$_2$, Cu(OAc)$_2$). The rearrangement of hydrazones of the general structure 4 to 1,2,3-triazoles of the general structure 1 is preferentially performed in the presence of either an inorganic base or a strong acid.

The rearrangement of hydrazones of the general structure 4 to 1,2,3-triazoles of the general structure 1 may be performed neat or in the presence of a solvent. In reactions where a solvent is used, solvents such as amides (e.g., DMF, DMAC), nitriles (e.g., MeCN, PrCN), alcohols (e.g., MeOH, EtOH, (i)-PrOH, (n)-BuOH), ethers (e.g., Et$_2$O, 2-methyl-tetrahydrofuran, THF, MTBE), esters (e.g., EtOAc, BuOAc), aromatic hydrocarbons or halogenated derivatives thereof (e.g., toluene, xylene, chlorobenzene), hydrocarbons or halogenated derivatives thereof (e.g., methylcyclohexane, heptane, dichloromethane, dichloroethane), sulfoxides (e.g., dimethylsulfoxide, sulfolane), ketones (e.g., acetone, methylisobutylketone), or water may be used either singly or as a mixture of two or more thereof. The use of nitriles, alcohols, water, or mixtures thereof is preferred. Especially preferred is the use of MeOH, (i)-PrOH, (n)-BuOH, MeCN, water, or mixtures of two or more of these solvents.

When the rearrangement is performed in a solvent or a mixture of solvents, the concentration of the hydrazone of general structure 4 in the resulting mixture may lie between 1%-50% (w/w), although a range from 5%-30% (w/w) is preferred.

If an activating agent is used, then the reaction stoichiometry between the hydrazone of structure 4 and the activating agent may range from 0.01 equiv. to 10 equiv., although a range from 0.05-5 equiv. is preferred.

The reaction may be carried out between −40° C. and 180° C., and is preferably carried out between −10° C. and 120° C.

The reaction may be carried out between 0.1 bar and 10 bar pressure, and is preferably carried out between 0.8 bar and 1.2 bar.

One skilled in the art will further be aware that hydrazones such as those represented by the general structure 4 can exist as E- or Z-isomers, and that these isomers can interconvert. The rearrangement reaction to 1,2,3-triazoles of the general structure 1 may be performed on one of these isomers in its pure form or on a mixture of the two stereoisomers.

In a more efficient embodiment of the invention, 1,2,3-triazoles of the general structure 1 can be prepared directly from an aldehyde of the general structure 12 in an two-step sequence involving a hydrazine of the general structure 13 (or a salt thereof) without isolation of the intermediate hydrazone of the general structure 4.

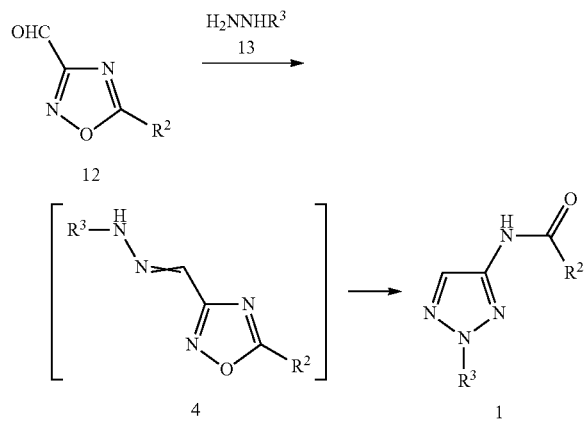

In an even more efficient embodiment of the invention, 1,2,3-triazoles of the general structure 1 can be prepared directly from a protected oxadiazole of the general structure 11 in an three-step sequence involving a hydrazine of the general structure 13 (or a salt thereof) without isolation of the corresponding aldehyde 12 or hydrazone 4.

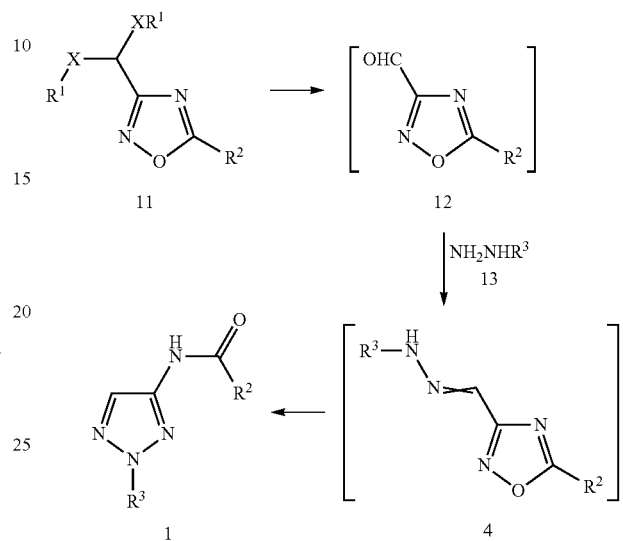

In addition to this process to 4-amido-1,2,3-triazoles of the general structure 1, we claim the preparation and use of the previously unreported acylated amidoximes of the general structure 10

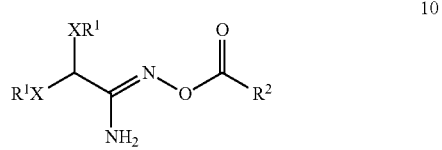

wherein X and R$^1$ have the same definitions as provided above for the preparation of compounds of the general structure 8, and;

R$^2$ is an alkyl, aromatic or heterocyclic group.

When R$^2$ is an alkyl group, it is a C$_{1-8}$-group (which may be straight-chained or branched), and may contain 1-17 groups chosen independently from the following list: halogens, C$_{1-8}$-alkoxy groups (which may be straight-chained, cyclic, or branched), C$_{1-8}$-alkylthio groups (which may be straight-chained, cyclic, or branched), nitriles, or groups of the structure C(=O)NR$^a$R$^b$ (where R$^a$ and R$^b$ are independently chosen between H or a C$_{1-4}$-alkyl group (which may be straight-chained or branched)). Alternatively R$^2$ is a C$_{3-6}$-carbocycle that can be substituted with 1-6 groups independently chosen from the following list: C$_{1-4}$-alkyl groups (which may be straight-chained, cyclic, or branched), C$_{1-4}$-alkoxy groups (which may be straight-chained, cyclic, or branched), halogens, C$_{1-4}$-alkoxycarbonyl groups (which may be straight-chained or branched), C$_{1-8}$-alkylthio groups (which may be straight-chained, cyclic, or branched), nitriles or groups of the structure C(=O)NR$^a$R$^b$ (where R$^a$ and R$^b$ are independently chosen between H or a C$_{1-4}$-alkyl group (which may be straight-chained or branched)).

When $R^2$ is an aromatic group, it is a phenyl, naphthyl, anthracenyl, phenanthrenyl, or pyrenyl group, and is unsubstituted or is substituted with 1-5 substituents independently chosen from the following list: $C_{1-8}$-alkyl groups (which may be straight-chained, cyclic, or branched), $C_{1-8}$-haloalkyl groups (which may be straight-chained, cyclic, or branched), $C_{1-8}$-alkoxy groups (which may be straight-chained, cyclic, or branched), $C_{1-8}$-alkylthio groups (which may be straight-chained, cyclic, or branched), halogens, nitro groups, nitrile groups, or groups of the structure $C(=O)NR^aR^b$ (where W and $R^b$ are independently chosen between H or a $C_{1-4}$-alkyl group (which may be straight-chained or branched)).

When $R^2$ is heterocyclic, it is a 4-, 5-, or 6-membered ring containing 1-4 heteroatoms independently chosen between O, N, and S. This heterocycle is unsubstituted or is substituted with 1-4 substituents independently chosen from the following list: $C_{1-8}$-alkyl groups (which may be straight-chained, cyclic, or branched), $C_{1-8}$-haloalkyl groups (which may be straight-chained, cyclic, or branched), $C_{1-8}$-alkoxy groups (which may be straight-chained, cyclic, or branched), $C_{1-8}$-alkylthio groups (which may be straight-chained, cyclic, or branched), nitriles, nitro groups, halogens, or groups of the structure $C(=O)NR^aR^b$ (where $R^a$ and $R^b$ are independently chosen between H or a $C_{1-4}$-alkyl group (which may be straight-chained or branched)).

In a preferred embodiment of the invention, X and $R^1$ have the same definitions as provided above for the preferred embodiment of the preparation of compounds of the general structure 8, and $R^2$ is an alkyl, aromatic or heterocyclic group.

When $R^2$ is an alkyl group, it is a $C_{1-4}$-group (which may be straight-chained or branched), and may contain 1-9 groups independently chosen from the following list: halogens, $C_{1-4}$-alkoxy groups (which may be straight-chained, cyclic, or branched), or groups of the structure $C(=O)NR^aR^b$ (where $R^a$ and $R^b$ are independently chosen between H or a $C_{1-4}$-alkyl group (which may be straight-chained or branched)). Alternatively $R^2$ is a $C_{3-6}$-carbocycle that can also be substituted with 1-4 groups independently chosen from the following list: $C_{1-4}$-alkyl groups (which may be straight-chained, cyclic, or branched), $C_{1-4}$-alkoxy groups (which may be straight-chained, cyclic, or branched), $C_{1-4}$-haloalkyl groups (which may be straight-chained, cyclic, or branched), or halogens.

When $R^2$ is an aromatic group, it is a phenyl, naphthyl, or anthracenyl group, and is unsubstituted or is substituted with 1-4 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), halogens, nitro groups, nitrile groups, or groups of the structure $C(=O)NR^aR^b$ (where $R^a$ and $R^b$ are independently chosen between H or a $C_{1-4}$-alkyl group (which may be straight-chained or branched)).

When $R^2$ is heterocyclic, it is a 4-, 5-, or 6-membered ring containing 1-4 heteroatoms independently chosen between O, N, and S, and is in particular selected from the group consisting of

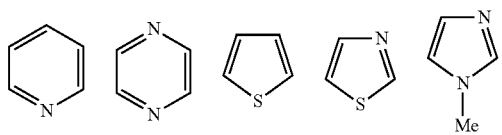

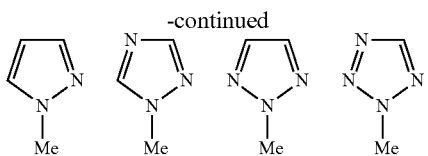

which may be connected to the rest of the molecule through any of the ring carbon atoms. This heterocycle is unsubstituted or is substituted with 1-3 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained or branched), nitriles, nitro groups, halogens, or groups of the structure $C(=O)NR^aR^b$ (where $R^a$ and $R^b$ are independently chosen between H or a $C_{1-4}$-alkyl group (which may be straight-chained or branched)).

In an especially preferred embodiment of the invention, X and $R^1$ have the same definitions as provided above for the especially preferred embodiment of the preparation of compounds of the structure 8, and $R^2$ is an alkyl, aromatic or heterocyclic group.

When $R^2$ is an alkyl group, it is a $C_{1-4}$-group (which may be straight-chained, cyclic, or branched), and may contain halogens. Alternatively $R^2$ is a $C_{3-6}$-carbocycle that can be substituted with 1-3 groups independently chosen from the following list: $C_{1-4}$-alkyl groups (which may be straight-chained, cyclic, or branched), $C_{1-4}$-alkoxy groups (which may be straight-chained, cyclic, or branched), $C_{1-4}$-haloalkyl groups (which may be straight-chained, cyclic, or branched), or halogens.

When $R^2$ is an aromatic group, it is a phenyl group, and is unsubstituted or is substituted with 1-3 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), halogens, nitro groups, nitrile groups.

When $R^2$ is heterocyclic, it is a pyridine ring; a pyrazine ring; a thiophene ring; a thiazole ring, or a 1-methylpyrazole ring. This heterocycle is unsubstituted or is substituted with 1-2 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), nitriles, or halogens.

Equally part of the invention is the preparation and use of the previously undescribed hydrazones of the structure of 4:

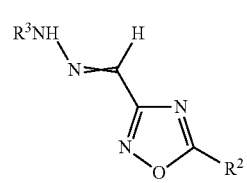

4 wherein $R^2$ has the same definition as provided above for the preparation of aldehydes of the general formula 12, and $R^3$ is an alkyl, aromatic or heterocyclic group.

When $R^3$ is an alkyl group, it is a $C_{1-8}$-group (which may be straight-chained or branched), and may contain 1-17 substituents independently chosen from the following list: $C_{1-4}$-alkoxy groups (which may be straight-chained, cyclic, or branched), halogen, or $C_{1-4}$-alkoxycarbonyl groups (which may be straight-chained or branched). Alternatively $R^3$ is a $C_{3-6}$-carbocycle that can be substituted with 1-5 groups independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), $C_{1-4}$-alkoxycarbonyl groups (which may be straight-chained or branched), or halogens.

When $R^3$ is an aromatic group, it is a phenyl, naphthyl, anthracenyl, phenanthrenyl, or pyrenyl group, and is unsubstituted or is substituted with 1-5 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), $C_{1-4}$-alkoxycarbonyl groups (which may be straight-chained or branched), groups of the structure $C(=O)NR^aR^b$ (where $R^a$ and $R^b$ are independently chosen between H or a $C_{1-4}$-alkyl group (which may be straight-chained or branched)), nitro groups, nitriles, or halogens.

When $R^3$ is heterocyclic, it is a 4-, 5-, or 6-membered ring containing 1-4 heteroatoms independently chosen between O, N, and S. This heterocycle is unsubstituted or is substituted with 1-4 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), $C_{1-4}$-alkoxycarbonyl groups (which may be straight-chained or branched), groups of the structure $C(=O)NR^aR^b$ (where $R^a$ and $R^b$ are independently chosen between H or a $C_{1-4}$-alkyl group (which may be straight-chained or branched)), nitro groups, nitriles, or halogens.

In a preferred embodiment of the invention $R^2$ has the same definitions as provided above for the preferred embodiment of the preparation of aldehydes of the general formula 12, and $R^3$ is an alkyl, aromatic or heterocyclic group.

When $R^3$ is an alkyl group, it is a $C_{1-4}$-group (which may be straight-chained or branched), and may contain 1-9 halogens. Alternatively it is a $C_{3-6}$-carbocycle that can be substituted with 1-3 groups independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), or halogens.

When $R^3$ is an aromatic group, it is a phenyl, naphthyl, or anthracenyl group, and is unsubstituted or is substituted with 1-4 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), nitro groups, nitriles, or halogens.

When $R^3$ is heterocyclic, it is a 4-, 5-, or 6-membered ring containing 1-4 heteroatoms independently chosen between O, N, and S, and is in particular selected from the group consisting of

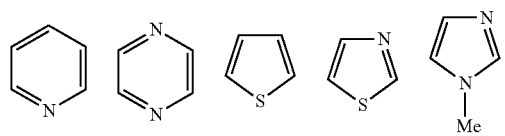

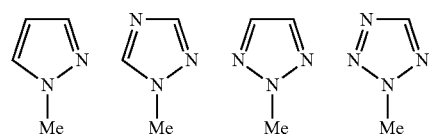

which may be connected to the rest of the molecule through any of the ring carbon atoms. This heterocycle is unsubstituted or is substituted with 1-3 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), nitro groups, nitriles, or halogens.

In an especially preferred embodiment of the invention $R^2$ has the same definitions as provided above for the especially preferred embodiment of the preparation of aldehydes of the general formula 12, and $R^3$ is an alkyl, aromatic, or heterocyclic group.

When $R^3$ is an alkyl group, it is a $C_{1-4}$-group (straight-chained or branched) and may contain 1-9 halogens. Alternatively it is a $C_{3-6}$-carbocycle that is unsubstituted or is substituted with 1-2 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), or halogens.

When $R^3$ is an aromatic group, it is an phenyl group, and is unsubstituted or is substituted with 1-3 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), nitro groups, nitriles, or halogens.

When $R^3$ is heterocyclic, it is a pyridine ring; a pyrazine ring; a thiophene ring; a thiazole ring, or a 1-methylpyrazole ring. This heterocycle is unsubstituted or is substituted with 1-2 substituents independently chosen from the following list: $C_{1-4}$-alkyl groups (which may be straight-chained, cyclic, or branched), $C_{1-4}$-haloalkyl groups (which may be straight-chained, cyclic, or branched), $C_{1-4}$-alkoxy groups (which may be straight-chained, cyclic, or branched), nitriles, or halogens.

One skilled in the art will further be aware that hydrazones of the general structure 4 can exist as E- or Z-isomers, and that these isomers can interconvert. If desired, these isomers can generally be separated by standard isolation techniques (e.g., chromatography, recrystallization, distillation). The present invention includes the preparation and use of either of these isomeric forms and mixtures thereof.

EXAMPLES

Abbreviations used:
RT=room temperature, Me=methyl, Et=ethyl, Ph=phenyl, h=hour(s), min=minute(s)

The present invention is illustrated in detail by the following examples, although the examples should not be interpreted in a manner that restricts the invention.

Example 1: Preparation of an Amidoxime of the General Structure 8: 2,2-Diethoxy-N'-hydroxyethanimidamide 8a

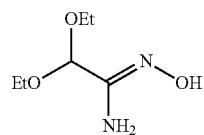

A solution of hydroxylamine hydrochloride (59.3 g, 827 mmol) and diethoxyacetonitrile (73.5 g, 551 mmol) in water (180 mL) and ethanol (360 mL) was treated portionwise at RT with solid $Na_2CO_3$ (45.6 g, 430 mmol). After 1 h the ethanol was removed from the mixture by distillation at reduced pressure. The resulting mixture was diluted with water (250 mL) and extracted with dichloromethane (1×300 mL, 2×100 mL). The combined organic extracts were dried ($Na_2SO_4$) and concentrated at reduced pressure to give the title compound as a white solid (87.0 g, 536 mmol, 97%). $^1$H NMR (400 MHz, $CD_3CN$): δ 7.51 (br s, 1H), 4.73 (br s, 2H), 4.62 (s, 1H), 3.55 (m, 4H), 1.17 (t, J=7.1 Hz, 6H).

Example 2: Acylation of an Amidoxime to Give a Compound of the General Structure 10: 2,2-diethoxy-N'-[(4-methoxybenzoy)oxy]ethanimidamide 10a

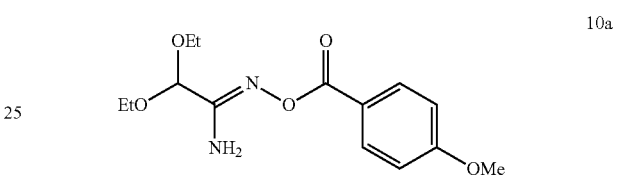

A solution of pyridine (6.44 g, 81.3 mmol) and 2,2-diethoxy-N'-hydroxyethanimidamide (12.0 g, 73.9 mmol) in $CH_2Cl_2$ (100 mL) was treated between 0-5° C. with a solution of 4-methoxybenzoyl chloride (13.4 g, 77.6 mmol) in $CH_2Cl_2$ (20 mL). The resulting mixture was brought to RT and stirred for 45 min before water (75 mL) was added. The phases were separated and the organic layer was washed with water (20 mL), dried ($Na_2SO_4$) and concentrated under reduced pressure to give the title compound as a beige solid (22.0 g, 95% purity, 70.6 mmol, 95%).

TABLE 1

Examples of acylated amidoximes of the general structure 10 prepared according to or in analogy to this procedure

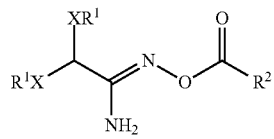

| Structure | X | $R^1$ | $R^2$ | Yield | $^1$H NMR ($CD_3CN$, 400 MHz) |
|---|---|---|---|---|---|
| 10a | O | Et | 4-MeOPh | 95% | 8.02 (d, J = 9 Hz, 2H), 7.00 (d, J = 9 Hz, 2H), 5.49 (br s, 2H), 4.85 (s, 1H), 3.86 (s, 3H) 3.70-3.50 (m, 4H), 1.21 (t, J = 7 Hz, 6H) |
| 10b | O | Et | 2-ClPh | 89% | 7.80 (m, 1H), 7.53 (m, 2H), 7.43 (m, 1H), 5.50 (br s, 2H), 4.86 (s, 1H), 3.70-3.50 (m, 4H), 1.21 (t, J = 7 Hz, 6H) |
| 10c | O | Et | 2-$CF_3$Ph | 97% | 7.83 (m, 2H), 7.73 (m, 2H), 5.46 (br s, 2H), 4.85 (s, 1H), 3.70-3.50 (m, 4H), 1.21 (t, J = 7 Hz, 6H) |
| 10d | O | Et | 2-Cl-3-pyridyl | 92% | 8.52 (m, 1H), 8.19 (m, 1H), 7.46 (m, 1H), 5.55 (br s, 2H), 4.86 (s, 1H), 3.70-3.50 (m, 4H), 1.21 (t, J = 7 Hz, 6H) |
| 10e | O | Et | Me | 95% | 5.39 (br s, 2 H), 4.76 (s, 1H), 3.70-3.50 (m, 4H), 2.08 (s, 3H), 1.18 (t, J = 7 Hz, 6H) |

Example 3: Cyclization of an Acylated Amidoxime to a Protected 1,2,4-oxadiazole of the General Structure 11: 5-(4-methoxyphenyl)-3-(diethoxymethyl)-1,2,4-oxadiazole 11a

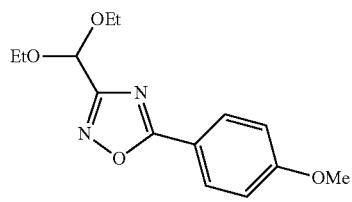

11a

A solution of 2,2-diethoxy-N'-[(4-methoxybenzoyl)oxy]-ethanimidamide (500 mg, 1.60 mmol) in toluene (4 mL) was treated with TBAF (1 M in THF, 320 μL, 0.320 mmol) and stirred overnight at 60° C. The resulting mixture was then cooled to RT, and washed with 10% NaOH (1 mL). The organic phase was separated and the remaining aqueous phase was extracted with toluene (2 mL). The combined organic phases were filtered through a pad of silica gel, dried (MgSO₄), and concentrated under reduced pressure to give the title compound as a colourless oil (400 mg, 98% purity, 1.41 mmol, 88%).

Example 4: Deprotection of a Protected 1,2,4-Oxadiazole to an Aldehyde of the General Structure 12: Preparation of 5-(4-methoxyphenyl)-1,2,4-oxadiazole-3-carbaldehyde 12a

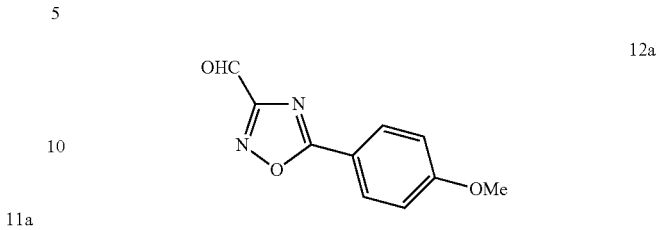

12a

A solution of 5-(4-methoxyphenyl)-3-(diethoxymethyl)-1,2,4-oxadiazole (13.0 g, 45.5 mmol) in MeCN (130 mL) was treated with 10% HCl (55 mL, 160 mmol) and stirred at 60° C. for 1.5 h. The majority of the acetonitrile was removed by distillation under reduced pressure and the resulting white suspension was diluted with water (130 mL), cooled to RT, and filtered. The filter cake was washed with water (20 mL) and dried overnight in a vacuum oven (50° C., 20 mbar) to give the title compound as a white solid (8.64 g, 42.3 mmol, 93%).

TABLE 3

Examples of aldehydes of the general structure 12 prepared according to or in analogy to this procedure

| Structure | R² | Yield | ¹H NMR (CD₃CN, 400 MHz) |
|---|---|---|---|
| 12a | 4-MeOPh | 93% | 10.09 (s, 1H), 8.14 (d, J = 8.9 Hz, 2H), 7.13 (d, J = 8.9 Hz, 2H), 3.9 (s, 3H) |
| 12b | 2-ClPh | 92% | 10.14 (s, 1H), 8.15 (d, J = 8.2 Hz, 1H), 7.68 (m, 2H), 7.56 (m, 1H) |

TABLE 2

Examples of 1,2,4-oxadiazoles of the general structure 11 prepared according to or in analogy to this procedure

| Structure | X | R¹ | R² | Yield | ¹H NMR (CD₃CN, 400 MHz) |
|---|---|---|---|---|---|
| 11a | O | Et | 4-MeOPh | 93% | 8.07 (d, J = 9 Hz, 2H), 7.10 (d, J = 9 Hz, 2H), 5.67 (s, 1H), 3.88 (s, 3H), 3.80-3.62 (m, 4H), 1.21 (t, J = 7 Hz, 6H) |
| 11b | O | Et | 2-ClPh | 98% | 8.08 (m, 1H), 7.64 (m, 2H), 7.52 (m, 1H), 5.74 (s, 1H), 3.82-3.65 (m, 4H), 1.23 (t, J = 1 Hz, 6H) |
| 11c | O | Et | 2-CF₃Ph | 93% | 8.03 (m, 1H), 7.96 (m, 1H), 7.86 (m, 2H), 5.75 (s, 1H), 3.71-3.65 (m, 4H), 1.22 (t, J = 7 Hz, 6H) |
| 11d | O | Et | 2-Cl-3-pyridyl | 91% | 8.62 (m, 1H), 8.45 (m, 1H), 7.56 (m, 1H), 5.76 (s, 1H), 3.72-3.57 (m, 4H), 1.23 (t, J = 7 Hz, 6H) |
| 11e | O | Et | Me | 87% | 5.59 (s, 1H), 3.75-3.58 (m, 4H), 2.55 (s, 3H), 1.18 (t, J = 7 Hz, 6H) |

TABLE 3-continued

Examples of aldehydes of the general structure 12 prepared according to or in analogy to this procedure

| Structure | R² | Yield | ¹H NMR (CD₃CN, 400 MHz) |
|---|---|---|---|
| 12c | 2-CF₃Ph | 99% | 10.13 (s, 1H), 8.10 (m, 1H), 8.04 (m, 1H), 7.88 (m, 2H) |

Example 5A: Condensation of an Aldehyde with a Hydrazine of the General Structure 13 to a Hydrazone of the General Structure 4: Preparation of 3-[((2,4-dichlorophenyl)hydrazono)methyl]-5-(4-methoxyphenyl)-1,2,4-oxadiazole 4a

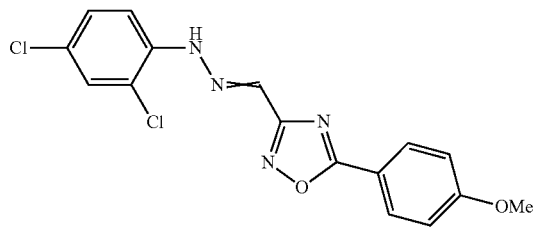

4a

A mixture of 5-(4-methoxyphenyl)-1,2,4-oxadiazole-3-carbaldehyde (500 mg, 2.40 mmol) and 2,4-dichlorophenylhydrazine (450 mg, 2.52 mmol) in MeCN (15 mL) was treated with 31% HCl (300 μL, 2.64 mmol) and stirred at RT for 3 h. The resulting white suspension was diluted with water (15 mL) and filtered. The filter cake was washed with water (10 mL) and dried overnight in a vacuum oven (50° C., 20 mbar) to give the title compound as a white solid (860 mg, 2.37 mmol, 99%, ca. 10:1 mixture of stereoisomers).

Example 5B: Condensation of an Aldehyde with a Salt of a Hydrazine of the General Structure 13 to a Hydrazone of the General Structure 4: Preparation of 2-(2-[[5-(4-methoxyphenyl)-1,2,4-oxadiazol-3-yl]methylene]hydrazino)-5-(trifluoromethyl)pyridine 4b

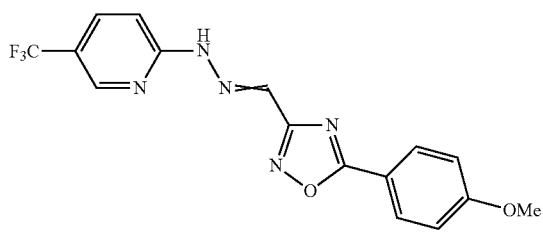

4b

A mixture of 5-(4-methoxyphenyl)-1,2,4-oxadiazole-3-carbaldehyde (500 mg, 2.40 mmol) and 2-hydrazino-5-(trifluoromethyl)pyridine hydrochloride (877 mg, 2.52 mmol) in MeCN (10 mL) was stirred at RT for 3 h. The resulting suspension was diluted with water (10 mL) and filtered. The filter cake was washed with water (10 mL) and dried overnight in a vacuum oven (50° C., 20 mbar) to give the title compound as a brown solid (630 mg, 1.73 mmol, 72%, ca. 90:10 mixture of stereoisomers).

Example 5C: Tandem Preparation of a Hydrazone of the General Structure 4 from a Protected Oxadiazole of the General Structure 11: Preparation of 2-[2-[(5-(6-chloropyridin-2-yl)-1,2,4-oxadiazol-3-yl)methylene]hydrazino]-5-(trifluoromethyl)-pyridine 4g

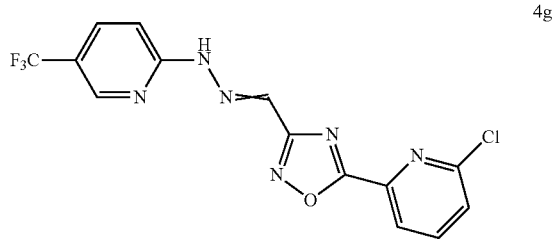 [SMILES: FC(F)(F)c1ccc(NN=Cc2noc(-c3cccc(Cl)n3)n2)nc1]

4g

A solution of 2-chloro-6-[3-(diethoxymethyl)-1,2,4-oxadiazol-5-yl]pyridine (750 mg, 2.58 mmol) in MeCN (10 mL) was treated with 10% HCl (3 mL, 9 mmol) and stirred at 85° C. for 3 h. The resulting solution was then cooled to RT and treated with 2-hydrazino-5-(trifluoromethyl)pyridine hydrochloride (943 mg, 2.71 mmol). After stirring for 1.5 h at RT the fine suspension was diluted with water (15 mL) and filtered. The filtercake was washed with water (10 mL) and dried at room temperature to give the title compound as a brown solid (790 mg, 92% purity, 1.97 mmol, 76%, >95:5 mixture of stereoisomers).

TABLE 4

Examples of hydrazonyl-1,2,4-oxadiazoles of the general structure 4 prepared according to or in analogy to these procedures

| Structure | R² | R³ | Yield | ¹H NMR |
|---|---|---|---|---|
| 4a | 4-MeOPh | 2,4-Cl$_2$Ph | 98% | 11.50 (s, 1H), 8.16 (d, J = 9 Hz, 2H), 7.68 (d, J = 2 Hz, 1H), 7.65 (s, 1H), 7.63 (d, J = 3 Hz, 1H), 7.44 (m, 1H), 7.24 (d, J = 9 Hz, 2H), 3.90 (s, 3H) |
| 4b | 4-MeOPh | 4-CF$_3$-2-pyridyl | 72% | 10.02 (s, 1H), 8.50 (s, 1H), 8.13 (d, J = 9 Hz, 2H), 8.04 (s, 1H), 7.95 (m, 1H), 7.42 (d, J = 9 Hz, 1H), 7.13 (d, J = 9 Hz, 2H), 3.90 (s, 3H) |
| 4c | 4-MeOPh | 6-Cl-2-pyridyl | >99% | 11.17 (s, 1H), 8.52 (s, 1H), 8.25 (m, 1H), 8.13 (d, J = 9 Hz, 2H), 7.86 (m, 1H), 7.20 (d, J = 9 Hz, 2H), 6.99 (m, 1H), 3.89 (s, 3H) |
| 4d | 4-MeOPh | Me | 65% | 8.08 (d, J = 9 Hz, 2H), 7.32 (s, 1H), 7.09 (m, 3H), 3.88 (s, 3H), 2.95 (s, 3H) |
| 4e | 2-CF$_3$Ph | Ph | 66% | Z-Isomer: 10.93 (s, 1H), 8.16 (m, 1H), 8.02 (m, 1H), 7.89 (m, 2H), 7.34 (m, 2H), 7.30 (s, 1H), 7.27 (m, 2H), 7.00 (m, 1H) E-Isomer: 9.42 (s, 1H), 8.07 (m, 1H), 7.98 (m, 1H), 7.87 (m, 2H), 7.83 (s, 1H), 7.30 (m, 2H), 7.14 (m, 2H), 6.94 (m, 1H) |
| 4f | 2-CF$_3$Ph | 2,6-F$_2$Ph | 58% | 11.84 (s, 1H), 8.45 (s, 1H), 7.87 (d, J = 8 Hz, 1H), 7.77 (m, 4H), 7.47 (t, J = 8 Hz, 2H) |
| 4g | 2-Cl-3-pyridyl | 4-CF$_3$-2-pyridyl | 76% | 10.06 (s, 1H), 8.64 (m, 1H), 8.51 (d, J = 2 Hz, 1H), 8.49 (d, J = 2 Hz, 1H), 8.08 (s, 1H), 7.95 (m, 1H), 7.58 (m, 1H), 7.41 (d, J = 9 Hz, 1H) |
| 4h | 2-ClPh | 2,4-Cl$_2$Ph | 85% | 11.35 (s, 1H), 8.19 (m, 1H), 7.68 (m, 3H), 7.58 (m, 1H), 7.50 (m, 2H), 7.35 (m, 1H) |

¹H NMR spectra were recorded at 400 MHz in CD$_3$CN except for examples 4a and 4f, which were recorded in DMSO-d$_6$. All hydrazones except example 4e were isolated with an isomeric purity of >90:10 as determined by ¹H NMR. The NMR data is reported for the major isomer of these examples; the exact structure of this major isomer has not been experimentally determined. Example 4e was isolated as a ca. 1:1 mixture of stereoisomers, the structures of which were determined after chromatographic separation.

Example 6A: Rearrangement of a hydrazonyl-1,2,4-Oxadiazole of the General Structure 4 to a 1,2,3-triazole of the General Structure 1 Under Basic Conditions: Preparation of N-[2-(2,4-dichlorophenyl)-2H-1,2,3-triazol-4-yl]-4-methoxybenzamide 1c

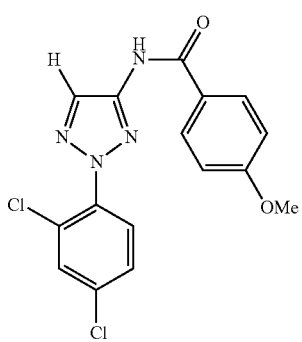

1c

A white suspension of 3-[(2,4-dichlorophenyl)carbonohydrazonoyl]-5-(4-methoxyphenyl)-1,2,4-oxadiazole (650 mg, 1.80 mmol) in (i)-PrOH (10 mL) was treated with 10%

NaOH (0.65 mL, 1.8 mmol), and the resulting light yellow suspension was stirred at 80° C. for 1 h. The solvents were then removed by distillation at reduced pressure, and the residue was taken up in water (5 mL) and extracted with CH$_2$Cl$_2$ (2×20 mL). The combined extracts were dried (MgSO$_4$), concentrated under reduced pressure, and dried overnight in a vacuum oven (50° C., 20 mbar) to give the title compound as a beige solid (610 mg, 1.65 mmol, 92%).

Example 6B: Rearrangement of a hydrazonyl-1,2,4-oxadiazole of the General Structure 4 to a 1,2,3-triazole of the General Structure 1 Under Acidic Conditions: Preparation of 4-methoxy-N-[2-[5-(trifluoromethyl)pyridin-2-yl]-2H-1,2,3-triazol-4-yl]benzamide 1d

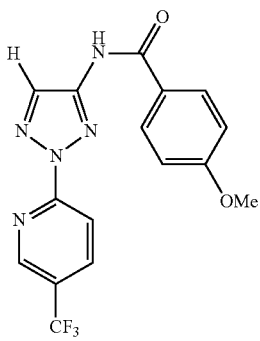

1d

A suspension of 2-[2-[(5-(4-methoxyphenyl)-1,2,4-oxadiazol-3-yl)methylene]hydrazine]-5-(trifluoromethyl)pyridine (10:1 mixture of stereoisomers, 620 mg, 1.70 mmol) in MeCN (10 mL) was treated with MeSO$_3$H (335 µL, 5.12 mmol) and stirred at 85° C. for 6 h. The resulting red suspension was cooled to RT, diluted with water (10 mL) and filtered. The filter cake was washed with water (5 mL) to give the title compound as a light brown solid (0.60 g, 1.6 mmol, 97%).

Example 6C: Rearrangement of a hydrazonyl-1,2,4-oxadiazole of the General Structure 4 to a 1,2,3-triazole of the General Structure 1 in the Presence of a Lewis Acid Catalyst: Preparation of N-[2-phenyl-2H-1,2,3-triazol-4-yl]-2-(trifluoromethyl)benzamide 1g

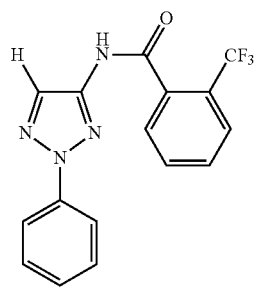

1g

A solution of 3-[(Z)-phenylhydrazonolmethyl]-5-[2-trifluoromethylphenyl]-1,2,4-oxadiazole (50 mg, 0.15 mmol) in MeOH (1 mL) was treated with Cu(OAc)$_2$ (3 mg, 0.02 mmol). After stirring for 3 h at RT the mixture was diluted with water (4 mL) and extracted with MTBE (15 mL). The organic phase was washed with water (5 mL), dried (Na$_2$SO$_4$) and concentrated under reduced pressure to give the title compound as a colourless oil (40 mg, 0.12 mmol, 83% yield).

Example 6D: Tandem Preparation of a 1,2,3-triazole of the General Structure 1 from an Aldehyde of the General Structure 12 without Isolation of the Intermediate Hydrazone: Preparation of N-[2-(2,6-difluorophenyl)-2H-1,2,3-triazol-4-yl]-2-(trifluoromethyl)-benzamide 1 h

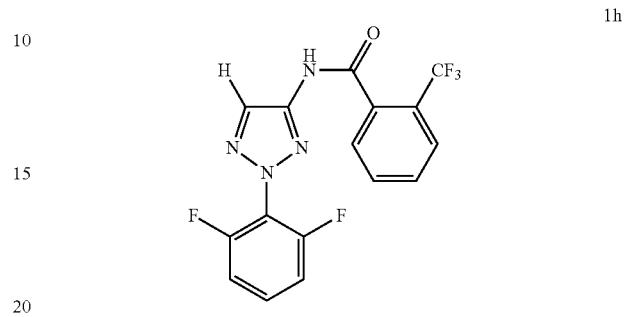

1h

A suspension of 5-(2-trifluoromethylphenyl)-1,2,4-oxadiazole-3-carbaldehyde (1.00 g, 3.88 mmol) and (2,6-difluorophenyl)hydrazinium chloride (0.817 g, 4.20 mmol) in acetonitrile (7.5 mL) was treated with 20% sulfuric acid (170 µL, 0.396 mmol) and stirred for 2 h at RT. The resulting solution (ca. 1:1 mixture of hydrazone stereoisomers) was then warmed to 50° C., treated with 32% NaOH (0.8 mL, 9 mmol) and stirred overnight. The resulting red solution was diluted with water (10 mL) and the acetonitrile was removed by distillation under reduced pressure. The resulting suspension was extracted with CH$_2$Cl$_2$ (1×50 mL, 1×10 mL), dried (MgSO$_4$) and purified by flash chromatography to give the title compound as a beige solid (1.20 g, 96% purity, 3.13 mmol, 81%).

Example 6E: Tandem Preparation of a 1,2,3-triazole of the General Structure 1 from a Protected Oxadiazole of the General Structure 11 without Isolation of the Intermediate Aldehyde or Hydrazone: Preparation of N-[2-(2,6-difluorophenyl)-2H-1,2,3-triazol-4-yl]acetamide 1k

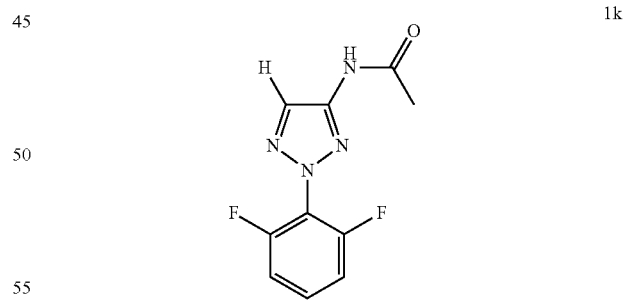

1k

A mixture of 5-methyl-3-(diethoxymethyl)-1,2,4-oxadiazole (102 mg, 0.545 mmol), (2,6-difluorophenyl)hydrazinium chloride (103 mg, 0.568 mmol) and 96% H$_2$SO$_4$ (5 µL, 0.09 mmol) in water (1 mL) was stirred at 80° C. for 3 h. The resulting yellow suspension was then treated with 10% NaOH (300 µL, 0.83 mmol) and (n)-BuOH (1 mL), and stirred at 80° C. for 1 h. The two phases were then separated and the aqueous phase was extracted with MTBE (3×1 mL). The combined organic phases were dried (Na$_2$SO$_4$) and concentrated under reduced pressure to give the title compound as a brown powder (114 mg, 0.478 mmol, 88%).

TABLE 5

Examples of 1,2,3-triazoles of the general structure 1 prepared according to or in analogy to these procedures

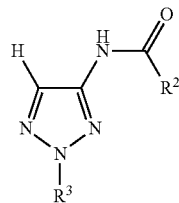

| Structure | $R^2$ | $R^3$ | Yield | $^1$H NMR (CD$_3$CN, 400 MHz) |
|---|---|---|---|---|
| 1c | 4-MeOPh | 2,4-Cl$_2$Ph | 92% | 9.45 (br s, 1H), 8.40 (s, 1H), 7.95 (d, J = 7 Hz, 2H), 7.71 (d, J = 2 Hz, 1H), 7.62 (d, 9 Hz, 1H), 7.51 (m, 1H), 7.04 (d, J = 9 Hz, 2H), 3.87 (s, 3H) |
| 1d | 4-MeOPh | 4-CF$_3$-2-pyridyl | 97% | 9.68 (br s, 1H), 8.86 (s, 1H), 8.51 (s, 1H), 8.24 (d, J = 2 Hz, 1H), 8.22 (d, J = 2 Hz, 1H), 7.99 (d, J = 9 Hz, 2H), 7.05 (d, J = 9 Hz, 2H), 3.88 (s, 3H) |
| 1e | 4-MeOPh | 6-Cl-2-pyridyl | 97% | 9.57 (br s, 1H), 8.53 (d, J = 4 Hz, 1H), 8.43 (s, 1H), 8.09 (m, 1H), 7.97 (d, J = 9 Hz, 2H), 7.56 (m, 1H), 7.04 (d, J = 9 Hz, 2H), 3.87 (s, 3H) |
| 1f | 4-MeOPh | Me | 68% | 9.22 (br s, 1H), 7.98 (s, 1H), 7.92 (d, J = 9 Hz, 2H), 7.02 (J = 9 Hz, 2H), 4.01 (s, 3H), 3.87 (s, 3H) |
| 1g | 2-CF$_3$Ph | Ph | 83% | 9.71 (br s, 1H), 8.33 (s, 1H), 7.99 (d, J = 8 Hz, 2H), 7.83 (d, J = 8 Hz, 1H), 7.71 (m, 3H), 7.52 (t, J = 8 Hz, 2H), 7.38 (t, J = 8 Hz, 1H) |
| 1h | 2-CF$_3$Ph | 2,6-F$_2$Ph | 81% | 9.68 (br s, 1H), 8.43 (s, 1H), 7.84 (d, J = 8 Hz, 1H), 7.73 (m, 3H), 7.62 (m, 1H), 7.25 (t, J = 8 Hz, 2H) |
| 1i | 2-Cl-3-pyridyl | 4-CF$_3$-2-pyridyl | 59% | 10.01 (s, 1H), 8.64 (m, 1H), 8.50 (m, 2H), 8.08 (m, 1H), 7.95 (m, 1H), 7.59 (m, 1H), 7.40 (d, J = 9 Hz, 1H) |
| 1j | 2-ClPh | 2,4-Cl$_2$Ph | 86% | 9.63 (br s, 1H), 8.39 (s, 1H), 7.72 (d, J = 2 Hz, 1H), 7.62 (d, J = 9 Hz, 2H), 7.53 (m, 3H), 7.46 (m, 1H) |
| 1k | Me | 2,6-F$_2$Ph | 88% | 9.12 (br s, 1H), 8.27 (s, 1H), 7.59 (m, 1H), 7.22 (m, 2H), 2.17 (s, 3H) |

The invention claimed is:

1. A process for preparation of one or more compounds of formula 1

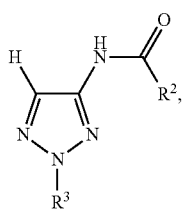

wherein $R^2$ is an alkyl, aromatic, or heterocyclic group, $R^3$ is phenyl substituted at 2- and 6-positions with substituents independently selected from the group consisting of C$_{1-4}$ alkyl, C$_{1-4}$ haloalkyl, C$_{1-4}$ alkoxy, nitro, nitrile, and halogen, by conversion of one or more compounds of formula 4 in which $R^2$ and $R^3$ have the above mentioned meanings, into one or more compounds of formula 1, wherein the conversion is effected in the presence of an activating agent, and wherein the activating agent is selected from the group consisting of NaOH, HCl, Cu(OAc)$_2$, and MeSO$_3$H.

2. The process according to claim 1, wherein
$R^2$ is 2-CF$_3$Ph, and
$R^3$ is 2,6-F$_2$Ph.

3. The process according to claim 1, wherein
$R^3$ is phenyl independently substituted at 2- and 6-positions with halogen.

4. The process according to claim 1, wherein
$R^3$ is 2,6-F$_2$Ph.

5. The process according to claim 1, wherein
$R^2$ is an aromatic group.

6. The process according to claim 1, wherein $R^2$ is 2-$CF_3$Ph.

7. The process according to claim 1, wherein the activating agent is NaOH.

8. The process according to claim 1, wherein the activating agent is HCl.

9. The process according to claim 1, wherein the activating agent is Cu(OAc)$_2$.

10. The process according to claim 1, wherein the activating agent is MeSO$_3$H.

* * * * *